United States Patent [19]

Seltzer et al.

[11] 4,137,139
[45] Jan. 30, 1979

[54] RADIATION CURABLE HYDANTOIN DIACRYLATE COMPOUNDS

[75] Inventors: Raymond Seltzer, New City; Joseph F. DiPrima, Hartsdale, both of N.Y.

[73] Assignee: Ciba-Geigy Corporation, Ardsley, N.Y.

[21] Appl. No.: 694,740

[22] Filed: Jun. 10, 1976

[51] Int. Cl.² .......................... C08F 2/46; C08F 4/00
[52] U.S. Cl. ...................... 204/159.23; 204/159.22; 260/239.3 R; 260/239.3 A; 260/836; 260/837 R; 427/44.54; 428/461; 526/264; 548/312
[58] Field of Search ...................... 204/159.23, 159.19, 204/159.22; 260/309.5, 239.3 R

[56] References Cited

U.S. PATENT DOCUMENTS

| 3,808,226 | 4/1974 | Habermeier | 260/309.5 |
| 3,821,098 | 6/1974 | Garratt et al. | 204/159.22 |

*Primary Examiner*—Richard B. Turer
*Attorney, Agent, or Firm*—Vincent J. Cavalieri; Joseph F. DiPrima

[57] ABSTRACT

Hydantoin diacrylate compounds of the formula

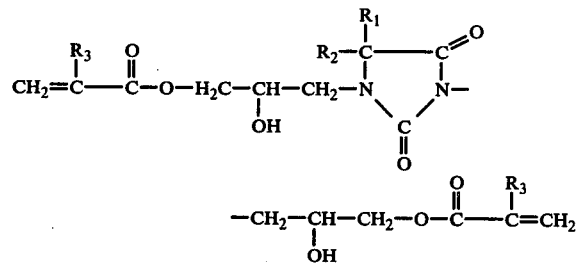

wherein $R_1$ is hydrogen, alkyl containing 1 to 8 carbon atoms; $R_2$ is alkyl containing 5 to 8 carbon atoms; and $R_3$ is hydrogen or methyl are prepared. The diacrylate compounds are liquid at room temperature, easily processable as adhesives, casting and laminating resins and when cured possess excellent resistance to water.

10 Claims, No Drawings

RADIATION CURABLE HYDANTOIN DIACRYLATE COMPOUNDS

DETAILED DESCRIPTION

This invention relates to novel hydantoin diacrylate compounds of the formula

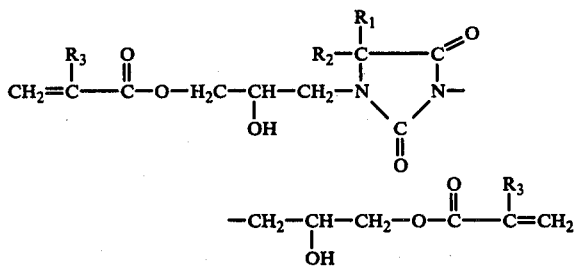

wherein $R_1$ is hydrogen, alkyl containing 1 to 8 carbon atoms, $R_2$ is alkyl containing 5 to 8 carbon atoms; and $R_3$ is hydrogen or methyl.

The alkyl group employed herein includes both straight- and branched-chain alkyl groups, examples of which are methyl, ethyl, propyl, isopropyl, butyl, isobutyl, pentyl, neopentyl, amyl, isoamyl, sec-amyl, hexyl, octyl and the like.

Preferably, $R_1$ is H, or alkyl containing 1 to 6 carbon atoms and $R_2$ is alkyl containing 5 to 6 carbon atoms.

Prior art hydantoin diacrylate compounds are disclosed in U.S. Pat. No. 3,808,226, which have the formula

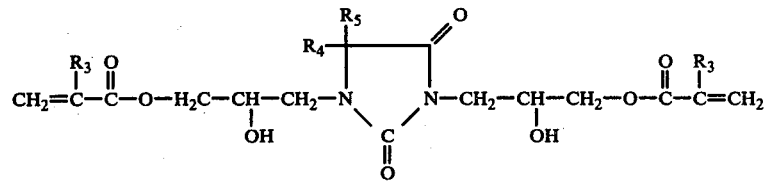

in which $R_4$ and $R_5$ each denote a hydrogen atom or a lower alkyl or alkenyl each having 1 to 4 carbon atoms, cycloalkyl or an optionally substituted phenyl, or in which $R_4$ and $R_5$ jointly form a tetramethylene or pentamethylene residue.

The hydantoin diacrylate compounds of this patent however, have the disadvantage of being crystalline solids or being highly viscous, and display poor resistance to water. Thus, the mechanical and electrical properties for these cured products rapidly decay on exposure to water or humidity, rendering them of little value in these applications.

The diacrylate hydantoin compounds of this invention having an alkyl group of 5 to 8 carbon atoms in the 5 position of the hydantoin ring have significant advantages over the "lower alkyl" examples described in the aforementioned patent. The compounds of this invention have generally lower viscosity which results in easier processing and are especially suitable as an adhesive, casting and laminating resin. The cured compounds have low dielectric constants which result in improved electrical properties and, of most significance, the cured compounds have greater water resistance.

The diacrylates of this invention are simply prepared by adding 2 equivalents of acrylic or methacrylic acid to the N,N'-diglycidyl resins.

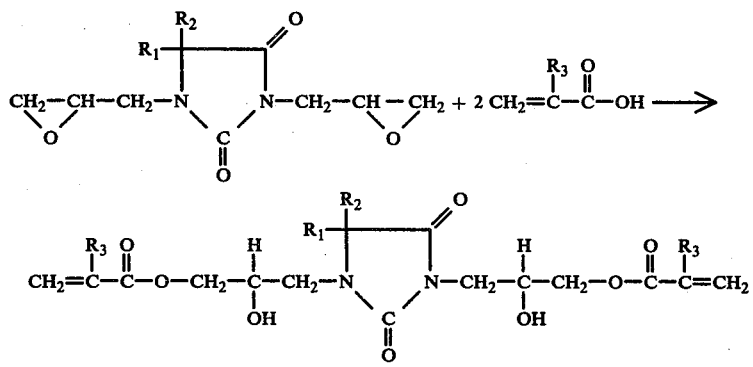

The intermediate hydantoins of the formula

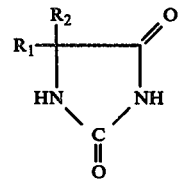

can be prepared by the well-known method of using a given ketone, sodium cyanide and ammonium carbonate. The diglycidyl hydantoins can then be prepared in the usual way using epichlorohydrin, tetramethylammonium chloride (TMAC) and alkali, e.g.,

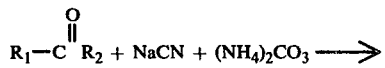

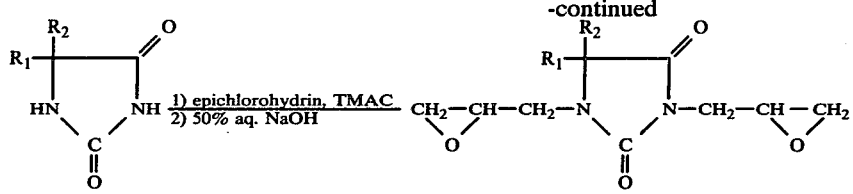

$R_1$, $R_2$ and $R_3$ in each of the above preparations are as hereinbefore defined.

The diacrylate hydantoin compounds of this invention are especially suitable for use as adhesives, casting and laminating resins and coatings. The curable diacrylates may be employed in the fields of adhesives, surface protection, the electrical industry, laminating processes and the building industry. More specifically, the diacrylate hydantoin compounds of this invention when combined with the appropriate curing agents or when photocured may be used as insulating compositions for electrical parts, as compositions to prepare printed circuit boards, can coatings, inks, as an adhesive and further, as compositions for the preparation of decorative laminates and flooring.

The diacrylate compounds according to the invention of their mixtures with other monomers and/or curing agents can be mixed, before curing, with customary modifiers, such as extenders, fillers and reinforcing agents, pigments, dyestuffs, plasticizers, flow control agents, agents for conferring thixotropy, flameproofing substances and mould release agents.

Suitable monomers which can be added to the diacrylate hydantoin compounds are, in particular, compounds of the acrylic acid series, such as esters from acrylic acid or methacrylic acid, and alcohols or phenols, e.g., methylacrylate, ethylacrylate, butylacrylate, dodecyacrylate, methylmethacrylate, acrylonitrile, methacrylonitrile, ethylene glycol dimethylacrylate, hexanediol diacrylate, pentaerythritol tricicrylate, trimethylolpropone triacetote. It is moreover possible to use other reactive olefinic unsaturated monomers, such as, e.g., styrene, divinylbenzene, n-vinylpyrrolidone, vinyl esters such vinyl acetate, allyl compounds such as diallylphthalate, and others.

As extenders, reinforcing agents, fillers and pigments which can be introduced into the curable mixtures according to the invention there may, for example, be mentioned: coal tar, bitumen, glass fibers, boron fibers, carbon fibers, cellulose, polyethylene powder, slate powder, aluminum oxide trihydrate, chalk powder, gypsum, antimony trioxide, bentones, silica aerogel, (AEROSIL), lithopone, baryte, titanium dioxide, carbon black, graphite, iron oxide or metal powders, such as aluminum powder or iron powder.

The diacrylate hydantoin compounds according to this invention react with the customary free radical type curing agents or are photocurable with ionizing rays such as ultra-violet light, gamma rays or electron beam radiation.

The polyacrylate mixtures exhibit good adhesiveness on the surface of the base material and coatings can therefore be produced without difficulty on metals, wood, plastics, glass, paper, leather, etc.

The curing of the diacrylate compounds and mixtures can be carried out with any form of ionizing radiation, such as with a high-energy electromagnetic radiation such as, e.g., with Roetgen or gamma radiation, as well as with accelerated electrons and ultra-violet radiation.

Using accelerated electrons, the process is performed with a mean electron energy of 50 KeV to 4,000 KeV. If it is required to cure thin layers, such as, e.g., coatings, then a mean electron energy of 50 to 600 KeV and a curing dose of 0.5 to 5.0 Megarad, preferably of 1.0 to 3.0 Megarad, are applied.

Using ultra-violet radiation, it is necessary to have a photoinitiator present with the diacrylate hydantoin compounds and their mixtures. The photoiniator absorbs the radiation to produce free radicals which initiate polymerization. Examples of photoinitiators which may be used are as follows: (a) benzoin and benzoin ethers such as the methyl, ethyl and butyl derivatives, e.g., 2,2-diethoxyacetophenone, (b) benzophenone in combination with a catalyst such as triethylamine, N,N'-dimethylbenzylamine, dimethylaminoethanol, N-methyl-diethanolamine, and (c) benzophenone plus Michler's Ketone.

The photoinitiators are present in a concentration of from 0.05% to 10% and preferably 3% to 5% based on the weight of the diacrylate hydantoin compounds and their mixtures.

The diacrylates and their mixtures can be advantageously subjected, before, during or after curing, additionally to a heat treatment, which leads in some cases to a promotion of cross-linking.

Curing is advantageously performed in the absence of oxygen. In order to effect this, a protective gas atmosphere, e.g., nitrogen, is used.

It is advantageous in some cases to add to the diacrylate and/or its mixture small amounts of a polymerization catalyst forming free radicals, such as, e.g., peroxides, azo compounds, or persulphates.

The customary catalysts which form free radicals may be used for the polymerization or copolymerization; there may be mentioned hydrazine derivatives, for example hydrazine hydrochloride, organometallic compounds, such as lead tetraethyl and, in particular, aliphatic azo compounds, such as, α,α'-azoisobutyrodinitrile and organic peroxides or persalts, such as, for example, peracetic acid, acetyl peroxide, chloroacetyl peroxide, trichloroacetyl peroxide, benzoyl peroxide, chlorobenzoyl peroxide, benzoyl acetyl peroxide, propionyl peroxide, fluorochloropropionyl peroxide, lauryl peroxide, cumene hydroperoxide, cyclohexanone hydroperoxide, tert.-butyl hydroperoxide, di-tert.-butyl peroxide, di-tert.-amyl peroxide and p-methane hydroperoxide, and also inorganic peroxide compounds, such as sodium peroxide, alkali percarbonates, alkali persulphates or alkali perborates, and especially hydrogen peroxide, which can advantageously replace the more expensive benzoyl peroxide. The amount added is chosen, in a known manner, in accordance with the desired course of the reaction or in accordance with the desired properties of the polymer; advantageously, about 0.05 to 10 percent by weight of the catalyst, calculated relative to the total weight of the diacrylate or diacrylate-monomer mixture, are employed, with the total amount of the catalyst being added either initially or in portions during the course of the polymerization.

In certain cases, cationic or anionic catalysts can also be used.

To further illustrate the nature of this invention and the processes employed in preparing and curing the diglycidyl hydantoin resins of this invention, the following examples are given below:

A. Preparation of Hydantoins 5-sec-Amyl-5-Ethylhydantoin

To a slurry of ammonium carbonate (865 parts), sodium cyanide (180 parts) in water (1200 parts) was added 5-methyl-3-heptanone (385 parts) in ethanol (1200 parts) at ambient temperature with stirring. The reaction mixture was heated to 55° C. over a period of 30 minutes and maintained at 55° C. for 6 hours. After cooling to ambient temperature, chloroform (1000 parts) was added and the mixture stirred for ten minutes. The reaction mixture was filtered and the filter cake washed with additional chloroform (500 parts). The organic phase was collected and the aqueous phase washed with additional chloroform (1000 parts) in two portions. The combined organic phase was evaporated to dryness yielding crude product. The resultant white solid was slurried in water (2000 parts), filtered and dried to constant weight to afford 5-sec-amyl-5-ethylhydantoin (560 parts, 94% yield, mp 151°–6° C.).

Cal'c C, 60.58; H, 9.15; N, 14.13 Found C, 60.54; H, 9.44; N, 14.04

The following hydantoin were prepared employing the above procedure:
5-n-Amyl-5-methylhydantoin (Mp 101°–3° C., 94%)
5-i-Amyl-5-methylhydantoin (Mp 158°–161° C., 90%)
5-n-Hexyl-5-methylhydantoin (Mp 107°–110° C., 96%)
In a similar manner, by substituting the appropriate ketone or aldehyde for the 5-methyl-3-heptanone in the above example, the following hydantoin compounds are obtained:
5-amylhydantoin
5-hexyl-5-ethylhydantoin
5-octylhydantoin
5-heptyl-5-methylhydantoin
5-octyl-5-amylhydantoin
5,5-dioctylhydantoin

B. Preparation of Hydantoin Glycidyl Resins 1,3-Diglycidyl-5-sec-Amyl-5-Ethylhydantoin A mixture of 5-sec-amyl-5-ethylhydantoin (397 parts), epichlorohydrin (1575 parts) and tetramethylammonium chloride (10 parts) was heated slowly to 80° C. over a period of one hour and maintained at 80° C. for 2.5 hours. The reaction mixture was cooled to 60° C. and a reflux was established by reducing pressure. Fifty percent aqueous sodium hydroxide (416 parts) was added dropwise over 2.5 hours while water was removed azeotropically by a circulatory distillation. The reaction mixture was cooled to 40° C., filtered and the filter cake washed with additional epichlorohydrin (500 parts). The filtrate was treated with activated charcoal (2 parts) and filtered through a pad of filter aid. The filtrate was concentrated to near dryness to yield the crude resin. The resin was diluted with chloroform (2000 parts) and washed with water (1000 parts). The organic phase was dried with magnesium sulfate (250 parts), filtered and concentrated to dryness to afford 584 parts (94% yield) of 1,3-diglycidyl-5-sec-amyl-5-ethylhydantoin as a pale yellow resin; epoxy value of 6.18 eq/kg (96% of theory), Cl, 0.75%.

The following resins were also prepared following the above procedure.

| Resin | Yield | Epoxy Value eq/Kg | %Cl |
|---|---|---|---|
| 1,3-Diglycidyl-5-Amyl-5-Methylhydantoin | 100% | 6.70 (99%) | 0.80 |
| 1,3-Diglycidyl-5-i-Amyl-5-Methylhydantoin | 93% | 6.51 (97%) | 0.65 |
| 1,3-Diglycidyl-5-n-Hexyl-5-Methylhydantoin | 90% | 6.33 (98%) | 0.61 |

In a similar manner, by substituting the appropriate hydantoin for the 5-sec-amyl-5-ethylhydantoin in the above example, the following diglycidyl hydantoin compounds are obtained:
1,3-Diglycidyl-5-amylhydantoin
1,3-Diglycidyl-5-hexyl-5-ethylhydantoin
1,3-Diglycidyl-5-octylhydantoin
1,3-Diglycidyl-5-heptyl-5-methylhydantoin
1,3-Diglycidyl-5-octyl-5-amylhydantoin
1,3-Diglycidyl-5,5-di-n-octylhydantoin

C. Preparation of Diacrylates

EXAMPLE 1

Preparation of 1,3-Bis(3'-acryloxy-2'-hydroxypropyl)-5-sec-amyl-5-ethylhydantoin Into a one-liter resin kettle equipped with stirrer, thermometer, reflux condenser and dropping funnel, was added 174 g. of 1,3-diglycidyl-5-sec-amyl-5-ethylhydantoin having an epoxide content of 6.17 equiv./kg. (1.07 Moles). The pale yellow liquid resin was heated to 90° C. with stirring and 0.2 g. of hydroquinone was added. 82.2 g. of acrylic acid (1.14 Moles) was added dropwise over 1.5 hours while increasing the internal reaction temperature to 125° C. The reaction mixture was stirred for 6 hours at 125° C. at which point air was bubbled through the product for 45 minutes to remove the excess acrylic acid. The resulting pale yellow liquid resin had a residual epoxide content of 0.48 equiv./kg. and an acrylate content of 4.33 equiv./kg. corresponding to 95% of the desired product. The Gardner viscosity of this product is Z7 (38,000 cks).

In a similar manner, by substituting the following diglycidyl hydantoins for the 1,3-diglycidyl-5-sec-amyl-5-ethylhydantoin in Example 1:
1,3-Diglycidyl-5-amylhydantoin
1,3-Diglycidyl-5-hexyl-5-ethylhydantoin
1,3-Diglycidyl-5-octylhydantoin
1,3-Diglycidyl-5-heptyl-5-methylhydantoin
1,3-Diglycidyl-5-octyl-5-amylhydantoin
1,3-Diglycidyl-5,5-di-n-octylhydantoin
there are obtained the following diacrylate hydantoin compounds:
1,3-bis(3'-acryloxy-2'-hydroxypropyl)-5-amylhydantoin
1,3-bis(3'-acryloxy-2-hydroxypropyl)-5-hexyl-5-ethylhydantoin
1,3-bis(3'-acryloxy-2'-hydroxypropyl)-5-octylhydantoin
1,3-bis(3'-acryloxy-2'-hydroxypropyl)-5-heptyl-5-methylhydantoin
1,3-bis(3'-acryloxy-2'-hydroxypropyl)-5-octyl-5-amylhydantoin
1,3-bis(3'-acryloxy-2-hydroxypropyl)-5,5-n-octylhydantoin

EXAMPLE 2

Preparation of 1,3-Bis(3'-methacryloxy-2'-hydroxypropyl)-5-sec-amyl-5-ethylhydantoin 175 g. of the 1,3-diglycidyl-5-sec-amyl-5-ethylhydantoin used in Example 1, containing 6.17 equiv./kg. (1.08 Moles) with 0.2 g. of hydroquinone reacts with 97.7 g. of methacrylic acid (1.14 Moles) at 125° C. analogously to Example 1 to afford the desired product.

EXAMPLE 3

Preparation of 1,3-Bis(3'-acryloxy-2'-hydroxypropyl)-5-amyl-5-methylhydantoin 150 g. of 1,3-diglycidyl-5-amyl-5-methylhydantoin having an epoxide content of 6.70 equiv./kg. (1.01 Moles), with 0.2 g. of hydroquinone reacts with 76.0 g. of acrylic acid (1.05 Moles) at 125° C. analogously to Example 1 to afford the desired product.

EXAMPLE 4

Preparation of 1,3-Bis(3'-acryloxy-2'-hydroxypropyl)-5-hexyl-5-methylhydantoin 158 g. of 1,3-diglycidyl-5-hexyl-5-methylhydantoin, having an epoxide content of 6.33 equiv./kg. (1.00 Moles) with 0.2 g. of hydroquinone reacts with 76.0 g. of acrylic acid (1.05 Moles) at 125° C. analogously to Example 1 to afford the desired product.

D. Curing Examples

EXAMPLE 1

Ultraviolet Light Induced Polymerization of Higher Alkyl Hydantoin Diacrylates 60 parts of the diacrylate manufactured according to Example 1 was mixed with 40 parts of N-vinyl-2-pyrrolidone, and 3 parts of the photoinitiator butyl benzoin ether to afford a low viscosity pale yellow solution. A film of this solution on aluminum was irradiated for 2 seconds by a 200 watt/m² medium pressure mercury vapor lamp at a distance of 3 inches to afford a hard, tack free, solvent resistant coating.

EXAMPLE 2

Peroxide Induced Polymerization of Higher Alkyl Hydantoin Diacrylates 100 parts of the diacrylate manufactured according to Example 1 is stirred at 70° C. with 1.5 parts of 50% strength cyclohexanone hydroperoxide and polymerizes over the course of 2 hours/80° C. and 12 hours/120° C. in an aluminum mold to afford tough, solvent resistant plaque.

What is claimed is:

1. An hydantoin diacrylate compound of the formula

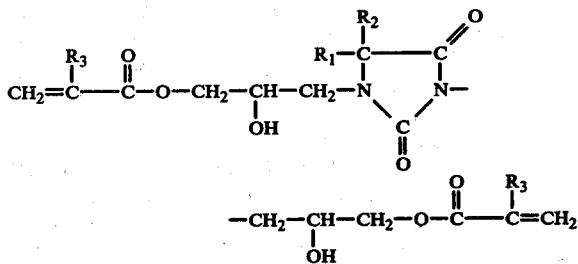

wherein $R_1$ is hydrogen, alkyl containing 1 to 8 carbon atoms; $R_2$ is alkyl containing 5 to 8 carbon atoms; and $R_3$ is hydrogen or methyl.

2. The compound of claim 1 wherein $R_1$ is hydrogen or alkyl containing 1 to 8 carbon atoms; and $R_2$ is alkyl containing 5 to 8 carbon atoms.

3. The compound of claim 1 wherein $R_1$ is methyl; $R_2$ is n-amyl; and $R_3$ is hydrogen.

4. The compound of claim 1 wherein $R_1$ is ethyl; $R_2$ is sec-amyl; and $R_3$ is hydrogen.

5. The compound of claim 1 wherein $R_1$ is ethyl; $R_2$ is sec-amyl; and $R_3$ is methyl.

6. The compound of claim 1 wherein $R_1$ is methyl; $R_2$ is n-hexyl; and $R_3$ is hydrogen.

7. A composition comprising the compound of claim 1 and a curing agent.

8. A composition comprising the compound of claim 1 and a photoinitiator.

9. A method of curing the compound of claim 1 by irradiating said compound with ionizing radiation.

10. The method of curing the composition of claim 8 by irradiating said composition with ultra-violet radiation.

* * * * *